United States Patent [19]

Dattagupta et al.

[11] Patent Number: 4,542,102
[45] Date of Patent: Sep. 17, 1985

[54] COUPLING OF NUCLEIC ACIDS TO SOLID SUPPORT BY PHOTOCHEMICAL METHODS

[75] Inventors: Nanibhushan Dattagupta, New Haven; Donald M. Crothers, Northford, both of Conn.

[73] Assignee: Molecular Diagnostics, Inc.

[21] Appl. No.: 511,064

[22] Filed: Jul. 5, 1983

[51] Int. Cl.$^4$ .............................................. G01N 33/50
[52] U.S. Cl. ........................................ 435/6; 422/57; 436/63; 436/94; 935/78
[58] Field of Search ................ 435/6; 422/57; 436/63, 436/94

[56] References Cited

U.S. PATENT DOCUMENTS 4,302,204 11/1981 Wahl .................................... 435/6 X
4,358,535 11/1982 Falkow ................................ 435/6 X

OTHER PUBLICATIONS

Chemical Abstracts I, 86:134373h, (1977).
Chemical Abstracts II, 88:69689r, (1978).
Chemical Abstracts III, 96:31231n, (1982).
Chemical Abstracts IV, 97:195359g, (1982).

*Primary Examiner*—Sidney Marantz
*Attorney, Agent, or Firm*—Sprung, Horn, Kramer & Woods

[57] ABSTRACT

A solid support capable of binding a nucleic acid thereto upon suitable irradiation, comprising (a) a solid substrate, (b) a member selected from the group consisting of a furocoumarin, a phenanthridium halide, and photochemically reactive derivatives thereof, and (c) a divalent radical chemically linking the substrate and the member (b). Specifically, a hydroxy group-containing solid substrate such as nitrocellulose paper is linked via a bifunctional reagent such as cyanogen bromide or 1,4-butanediol diglycidyl ether to an amino-substituted angelicin or psoralen or phenanthridinium bromide which in turn is photochemically linked to a nucleic acid. This is capable of hybridizing with other nucleic acid fragments and is thereby useful in diagnostic assays.

16 Claims, No Drawings

COUPLING OF NUCLEIC ACIDS TO SOLID SUPPORT BY PHOTOCHEMICAL METHODS

The present invention relates to a novel way of joining a nucleic acid to a solid substrate so as to provide a solid probe suitable for use in various tests.

For DNA-DNA hybridization and DNA-RNA hybridization one of the complementary nucleic acid chains should be coupled to a solid support. This helps to reduce the background and can be used to separate or isolate the corresponding nucleic acid. The methods of attachment of DNA to a solid support have involved (1) non-specific physical adsorption of a single-stranded DNA to nitrocellulose papers, (2) covalent attachment via diazo coupling. Both methods are specific for single-stranded DNA. These covalent reactions are non-specific and several sites are coupled. These cause inefficient hybridization and loss of perfect fidelity. Several points of attachment per chain reduces the flexibility of the DNA and reduces the rate of hybridization. Moreover, the lifetime of such an adduct is not very long. The DNA comes off easily and it is difficult to quantify the amount on the solid support, without the use of radioactivity. The use of DNA probes for diagnostic purposes demands an efficient method of tagging the DNA to a phase which can be separated easily from the rest of the nucleic acids.

Application Ser. No. 511,063, filed July 5, 1983, discloses various tests for nucleic acids, e.g., DNA of individuals being tested for sickle cell anemia. The test involves a soluble labelled probe and a probe fixed to a solid support. The probe can be fixed to the support chemically as by a bifunctional reagent which at one end reacts with the support, e.g., a hydroxyl group of a cellulose molecule, and at the other end reacts with the DNA. This is quite satisfactory for many purposes but in some instances there may be too much bonding between the substrate and DNA, impairing the sensitivity of the DNA in the test.

It is accordingly an object of the present invention to provide a way of binding a nucleic acid to a solid substrate easily and without impairment of the nucleic acid's ability to hybridize in later tests.

These and other objects and advantages are realized in accordance with the present invention wherein certain specific reagents are utilized to bind the nucleic acid to the substrate photochemically.

The specific reagents employed are amino-substituted furocoumarins, e.g., amino-methyl-dimethyl-angelicin and amino-methyl-trimethyl-psoralen, and amino-phenanthridinium halides as well as closely related chemical derivatives thereof. Upon photoactivation these reagents will chemically link with nucleic acids. These reagents have some site other than the nucleic acid-reactive site and, by such other site, they are joined to a solid substrate, thereby in turn joining the nucleic acid to such substrate with a minimum impairment of the nucleic acid function.

Angelicin, more accurately 4'aminomethyl-4,5'-dimethylangelicin, has the structural formula

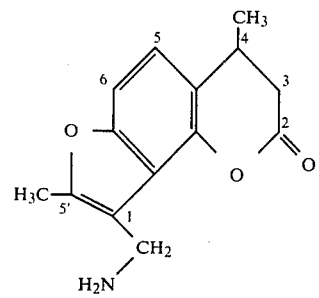

(see Dall'Acquz et al Photochemistry and Photobiology Vol. 37, No. 4, pp. 373–379, 1983.)

Psoralen, more accurately 4'aminomethyl-4,5',8-trimethyl-psoralen (AMT) has the structural formula

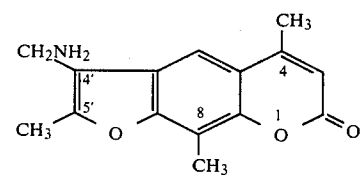

(Cadet et al Photochemistry and Photobiology Vol. 37, No. 4, pp. 363–371, 1983.)

Methidium chloride, for example, has the formula

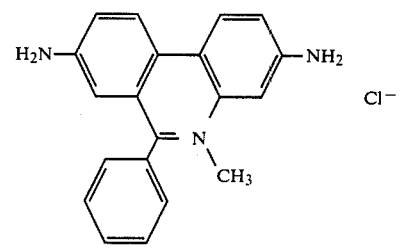

(see Graves et al Biochemistry 1981, Vol. 20, pp. 1887–1892.) Its mono- and di-azide analogues, shown below, are comparably reactive:

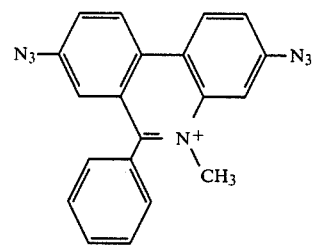

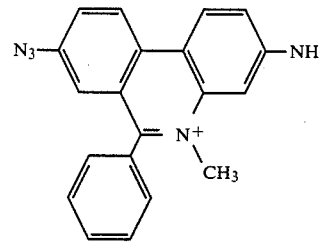

as are the ethyl counterparts and the aminopropyl derivative of the phenyl side chain (methidium propylamine) [see Hertzberg and Dervan, J. Am. Chem. Soc., Vol. 104, p. 313 (1982)].

The solid substrate can be any solid which has reactive groups which could be carboxyl, amino or the like, but the preferred reactive groups are hydroxyl such as are found on cellulose. The cellulose may be unmodified as in cotton or paper or regenerated as in rayon or partially esterified as in cellulose acetate, cellulose propionate and especially cellulose nitrate, or partially etherified as in methylcellulose and carboxymethylcellulose.

While the photochemically active reagent could be directly combined with the solid substrate, advantageously there is a mutual coupler which makes the connection. Suitable reagents include bifunctional compounds such as cyanogen bromide (CNBr), 1,4-butanediol digylcidyl ether, and the like. These are reacted with both the solid substrate and the photochemical reagent simultaneously or first with one and then with the other.

Thereafter the product is further reacted with the nucleic acid photochemically. The reactions with the coupler and nucleic acid are substantially quantitative so the quantities of the reagents employed depend upon the desired ratio of nucleic acid to solid support. For most purposes about 0.1 to 1000 mg and preferably about 1 to 100 mg of nucleic acid per gram of solid support will be suitable although it may be higher or lower, depending upon the molecular weight of the nucleic acid, its sensitivity and the particular test in which it is to be used.

The reaction conditions in each step are generally known per se and any solvents and temperatures can be employed which permit the reactions to proceed without interference, e.g., from about $-10°$ to $100°$ C., preferably about $10°$ to $50°$ C. and most preferably room temperature, employing inert organic solvents such as ether, carbon tetrachloride, THF and the like.

The photochemically active reagents herein employed preferably react through amino groups. Identifying it as $RNH_2$ and the substrate with pendent OH groups as Ⓢ, the stepwise reactions are as follows:

(a) with CNBr            A.

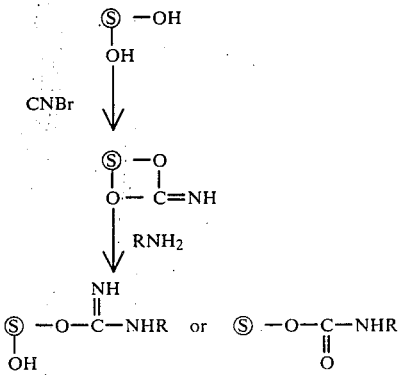

(b) 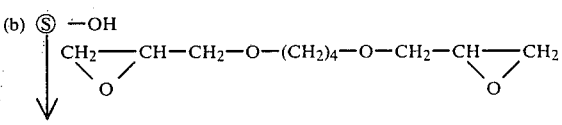

-continued

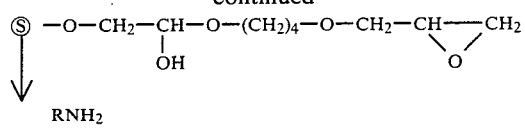

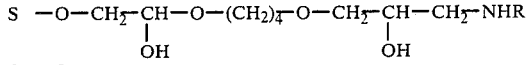

Amino-derivatives of angelicin and psoralen react correspondingly if not identically.

The particular wavelength of radiation selected will depend upon the particular photoreagent and whether it is desired to bind to a single strand of nucleic acid or to a double strand. If to both strands it can be in a manner and to a degree that the nucleic acid is no longer denaturable.

The nucleic acid can be RNA or DNA of short (oligonucleotide) or long chain length, as desired, doubly or singly stranded.

Formation of monoadducts is desirable for hybridization experiments. In crosslinks, both DNA strands are covalently linked to psoralen chromophore and hence strand separation prior to hybridization is difficult. If the probe to be hybridized is linked to another non-specific piece of DNA, the non-specific part can be linked either via crosslink or monoadduct formation. In that case irradiation can be done at any wavelength between 300–390 nm. Irradiation at 390 nm produces monoadduct, irradiation at 360–300 nm produces both monoadduct and crosslinks.

If angelicin compounds are used, the product will predominantly be monoadduct irrespective of the wavelength of irradiation.

The invention will now be further described with reference to the accompanying examples wherein all parts are by weight unless otherwise expressed.

EXAMPLE

1. Activation of the solid support and coupling of AMT.

The procedure described below has been followed for sephadex G25 and cellulose, but any hydroxy-containing solid support can be activated by an identical procedure.

(a) Activation with 1,4 butane-diol-diglycidyl ether. 0.5–1 gm solid powder is swollen with water and washed, then 5–10 ml sodium hydroxide solution (0.5 M) is added. To this thick suspension 1 ml 1,4-butanediol-diglycidyl ether (BDGE) is added. The suspension is shaken overnight on a mechanical shaker and then washed with sodium hydroxide (0.5 M) solution and 1.0 ml 4'-aminomethyl-4,5',8-trimethyl-psoralen (2 mg/ml) in water is added, followed by enough 1 M sodium hydroxide to have a thick suspension. The suspension is then stirred gently for 24 hours at room temperature and excess unreacted residues are quenched with lysine.

The solid is then washed with water followed by the desired aqueous buffer solution for DNA coupling.

(b) For epoxidation of paper the identical procedure is followed with Whatman filter papers type 540, 1 and 541. The filter papers are taken on a watch glass or beaker cover (glass) and turned occasionally by hand. The rest of the procedure is the same as above.

(c) Activation by cyanogen bromide and coupling of AMT. Typical example with cellulose:

0.5 gm cellulose is swollen in 5.0 ml distilled water for one hour. The swollen gel is washed thoroughly with distilled water. Then it is taken in an erlenmeyer flask, ice-cooled distilled water is added to the swollen cellulose and the pH is adjusted between 10.5-11.0 with 5M sodium hydroxide solution. The flask with its contents is cooled in ice to avoid temperature rise above 15° C. 1 gm of solid cyanogenbromide is added to the cellulose and the solution is stirred for 30 minutes and pH maintained between 10.5-11.0 by NaOH. The suspension is washed with ice cold distilled water, water is removed by centrifugation and 20 ml ice cold potassium phosphate buffer (10 mM; pH-8.0) is added. The activated cellulose is kept in brown bottles (in small aliquots) at −20° C.

2-3 ml of swollen, activated gel is taken in a brown bottle and 0.7 ml AMT (2 mg/ml) is added and the mixture is shaken gently in the cold room. Excess activated residues are quenched with lysine. The solid is washed with aqueous buffer for DNA binding.

(d) For papers similar procedures have been followed with Whatman cellulose filter papers type 504, 1 and 541 quantitative papers. Care should be taken to avoid tearing of the papers.

(e) Parallel experiments with $^3H$ labelled aminomethylpsoralen or angelicin are used to estimate labelling efficiency.

2. Coupling of phenanthridinium compounds to a solid support and azide formation for photochemical coupling of DNA:

Activation of the solid supports is done by the method described above. As an example, Methidium propylamine (R. P. Herzberg and P. B. Dervan, JACS, 104, 313 (1982)) is coupled to the solid support, using identical buffer conditions as in 1. The isolated methidium containing solid support is then diazotized and azide derivative is made as follows. 1 gm cellulose or ($2\times 5$ cm$^2$) a sheet of activated paper containing methidium chloride is taken in 20 ml water, cooled in ice, 0.2 ml ice cold HCl is added; sodium azide (20 mg solid; 2x) is added. The vessel is cooled in ice and sodium nitrite solid (100 mg) is added. The reaction is allowed to proceed for 30 minutes, solid support is washed with the desired buffer. Coupling of DNA and hybridization are carried out the same way as described for aminomethyl-psoralen. Aminomethyl-dimethyl-angelicin can be similarly treated.

3. Photochemical coupling of DNA:

0.5 ml (~0.2−0.3 gm gel+buffer) activated solid powder or 0.8×1 cm$^2$ activated paper is taken in a 1 cm path length spectrophotometer cuvette. Adenovirus DNA (partially labelled with $^3H$) (concentration 25 μg/ml) in tris EDTA buffer (10 mM tris, 1 mM EDTA, pH=7.5) is added to the cuvette and irradiation is done at a desired wavelength for 30 minutes to two hours depending on the future needs. For AMT irradiation at 390 nm produces monoadduct whereas at 360-300 nm both monoadduct and crosslinks are formed. By altering the concentration and DNA sequence, crosslink to monoadduct formation can be modulated. After photoirradiation, the solid is washed and the radioactivity of the washings and the solid support is counted in a Beckman 7800 scintillation counter.

| Solid support | Typical Results | |
|---|---|---|
| | % Coupling | DNA Coupled μg |
| ~ 0.5 ml swollen support or 0.8 × 1 cm$^2$ control paper (No DNA) | — | — |
| BDGE treated paper | 80 | 20 |
| Cellulose cellex CNBR activated | 91.5 | 22.5 |
| Cellulose cellex BDGE activated | 93.4 | 22.5 |
| Sephadex G25 CNBr activated | 69.5 | 18.0 |

4. Assay for DNA-DNA hybridization of DNA photochemically coupled to the solid support: Andenovirus DNA is covalently coupled to the solid support as above and hybridization with $^3H$ labelled adenovirus DNA is done following the procedure of Noyes and Stark, Cell, 5, 301-310 (1975).

5. Use of phochemically coupled DNA for sickel cell diagnosis: The separation probe (Application Ser. No. Molecular Diagnostics 201) is coupled to the solid support by the method described above. Then the support with the coupled DNA is mixed with the unknown and the detection probe under hybridization condition—as in 4. The solid support is then tested for the presence of label. If radioactivity labelled detection probe is used, radioactivity is counted.

5a. AMT coupled DNA can be recovered as free DNA by irradiation at 260 nm. The product of 4 is irradiated at 260 nm is otherwise the same manner as in 3, whereupon the DNA uncouples from the solid support, entering the solvent medium, viz. aqueous buffer. Then the liquid is assayed for $^3H$.

It will be understood that the specification and examples are illustrative but not limitative of the present invention and that other embodiments within the spirit and scope of the invention will suggest themselves to those skilled in the art.

What is claimed is:

1. A solid support capable of binding a nucleic acid thereto upon suitable irradiation, comprising (a) a solid substrate, (b) a member selected from the group consisting of (1) a furocoumarin, (2) a phenanthridinium halide, and (3) photochemically reactive derivatives of (1) and (2), and (c) a divalent radical chemically linking the solid substrate (a) and the member (b).

2. The support according to claim 1, wherein the solid substrate (a) in free state has free OH groups through which it is linked by the divalent radical (c).

3. The support according to claim 1, wherein the solid substrate (a) is cellulose or a cellulose ester.

4. The support according to claim 1, wherein the divalent radical (c) is derived from cyanogen bromide.

5. The support according to claim 1, wherein the divalent radical (c) is derived from 1,4-butanediol diglycidyl ether.

6. The support according to claim 1, wherein (b) is an aminomethyl psoralen.

7. The support according to claim 1, wherein (b) is an aminomethyl angelicin.

8. The support according to claim 1, wherein (b) is a phenanthridinium (ethidium bromide halide compound) azide.

9. A hybridization probe comprising (a) a solid substrate, (b) a member selected from the group consisting of (1) a furocoumarin, (2) ethidium bromide, and (3) photochemically reactive derivatives of (1) and (2), (c)

a divalent radical chemically linking the solid substrate (a) and the member (b), and (d) a nucleic acid photochemically linked to member (b) and fixed thereby to the solid substrate (a).

10. The hybridization probe according to claim 9, wherein the solid substrate (a) in free state has free OH groups through which it is linked by the divalent radical (c).

11. The hybridization probe according to the claim 9, wherein the solid substrate (a) is cellulose or a cellulose ester.

12. The hybridization probe according to claim 9, wherein the divalent radical (c) is obtained by the activation by cyanogen bromide.

13. The hybridization probe according to claim 9, wherein the divalent radical (c) is derived from 1,4-butanediol diglycidyl ether.

14. The hybridization probe according to claim 9, wherein member (b) is psoralen or a derivative thereof.

15. The hybridization probe according to claim 9, wherein member (b) is angelicin or a derivative thereof.

16. The hybridization probe according to claim 9, wherein member (b) is phenanthridinium halide or a derivative thereof.

* * * * *

UNITED STATES PATENT AND TRADEMARK OFFICE
CERTIFICATE OF CORRECTION

PATENT NO. : 4,542,102
DATED : September 17, 1985
INVENTOR(S) : Nanibhushan Dattagupta, et al.

It is certified that error appears in the above-identified patent and that said Letters Patent is hereby corrected as shown below:

| | |
|---|---|
| Col. 2, line 57 | After structure insert --methidium monoazide-- |
| Col. 2, line 68 | After structure insert --methidium diazide-- |
| Col. 3, line 20 | Correct spelling of "diglycidyl" |
| Col. 4, lines 7 and 9 (2 instances) | Delete "S" and substitute --(S)-- |
| Col. 4, line 9 | After "(S)—NHR" insert -- → -- |
| Col. 4, line 30 | Delete "wavelength" and substitute --wavelengths-- |
| Col. 5, line 20 | Delete "504" and substitute --540-- |
| Col. 6, line 19 | Correct spelling of "sickle" |
| Col. 7, line 11 | Before "claim 9" delete "the" |

Signed and Sealed this

Twenty-eighth Day of January 1986

[SEAL]

Attest:

DONALD J. QUIGG

Attesting Officer

Commissioner of Patents and Trademarks